(12) United States Patent
Braun

(10) Patent No.: US 10,470,849 B2
(45) Date of Patent: Nov. 12, 2019

(54) STATIC SELF-LIGATING ORTHODONTIC BRACKET AND METHOD OF USING SAME

(71) Applicant: OVERJET LLC, Fairfield, CT (US)

(72) Inventor: Thomas F. Braun, Fairfield, CT (US)

(73) Assignee: OVERJET LLC, Fairfield, CT (US)

( * ) Notice: Subject to any disclaimer, the term of this patent is extended or adjusted under 35 U.S.C. 154(b) by 0 days.

(21) Appl. No.: 14/772,581

(22) PCT Filed: Feb. 25, 2014

(86) PCT No.: PCT/US2014/018150
§ 371 (c)(1),
(2) Date: Sep. 3, 2015

(87) PCT Pub. No.: WO2014/137654
PCT Pub. Date: Sep. 12, 2014

(65) Prior Publication Data
US 2016/0030139 A1    Feb. 4, 2016

Related U.S. Application Data

(60) Provisional application No. 61/774,888, filed on Mar. 8, 2013.

(51) Int. Cl.
*A61C 7/00* (2006.01)
*A61C 7/28* (2006.01)
(Continued)

(52) U.S. Cl.
CPC ............ *A61C 7/28* (2013.01); *A61C 7/12* (2013.01); *A61C 7/148* (2013.01)

(58) Field of Classification Search
CPC .... A61C 7/12; A61C 7/14; A61C 7/20; A61C 7/28; A61C 7/148; A61C 7/285
(Continued)

(56) References Cited

U.S. PATENT DOCUMENTS 5,474,447 A * 12/1995 Chikami ............ A61C 7/12
433/10
6,663,385 B2   12/2003 Tepper
(Continued)

FOREIGN PATENT DOCUMENTS

EP          1127554      8/2001
WO    WO 2010-014518    2/2010

OTHER PUBLICATIONS

PCT/US2014/018150, Written Opinion dated Jun. 3, 2014, 6 pages—English.
(Continued)

*Primary Examiner* — Nicholas D Lucchesi
(74) *Attorney, Agent, or Firm* — Andrew F. Young, Esq.; Lackenbach Siegel, LLP

(57) ABSTRACT

The invention relates to an orthodontic bracket system, wherein an orthodontic wire is held in an open channel or slot which receives an orthodontic wire without means of any type of applied ligature or any type of moving cover. Disclosed is a static self-ligating orthodontic bracket system for coupling a pre-tensioned arch wire with a tooth, wherein the bracket comprises a bracket body configured to be mounted to a tooth, an arch wire slot configured for receiving a pre-tensioned arch wire therein, the arch wire slot configured with a at least one protruding stop or protuberance on an interior wall surface thereof, the stops spaced apart from one another, and a slot opening for receiving the arch wire into the arch wire slot, the opening having a width less than a diameter of the arch wire slot, wherein the arch wire is configured with a non-spherical cross-section.

14 Claims, 8 Drawing Sheets

(51) Int. Cl.
*A61C 7/12* (2006.01)
*A61C 7/14* (2006.01)

(58) Field of Classification Search
USPC .................................................. 433/8–17
See application file for complete search history.

(56) References Cited

U.S. PATENT DOCUMENTS

| | | | | |
|---|---|---|---|---|
| 7,175,428 B2* | 2/2007 | Nicholson | ............... | A61C 7/30 433/10 |
| 2001/0029008 A1* | 10/2001 | Jordan | ..................... | A61C 7/02 433/10 |
| 2003/0118967 A1* | 6/2003 | Tepper | ..................... | A61C 7/14 433/11 |
| 2005/0069833 A1 | 3/2005 | Chikami | | |
| 2006/0199137 A1* | 9/2006 | Abels | ....................... | A61C 7/12 433/11 |
| 2007/0207436 A1* | 9/2007 | Tan | ......................... | A61C 7/14 433/10 |
| 2010/0285418 A1* | 11/2010 | Trimmer | ................... | A61C 7/28 433/3 |
| 2011/0014583 A1* | 1/2011 | Romano | ................ | A61C 7/143 433/10 |
| 2011/0143301 A1* | 6/2011 | Maijer | ..................... | A61C 7/28 433/11 |
| 2012/0129122 A1* | 5/2012 | Carriere Lluch | ........ | A61C 7/14 433/17 |
| 2012/0225398 A1* | 9/2012 | Fallah | ..................... | A61C 7/12 433/8 |
| 2013/0309624 A1* | 11/2013 | Smith | .................... | A61C 7/285 433/9 |

OTHER PUBLICATIONS

PCT/US2014/018150, International Preliminary Report on Patentability, dated Sep. 8, 2015, 1 page—English.
PCT/US2014/018150, International Search Report dated Jun. 3, 2014, 3 pages—English.
Prov. U.S. Appl. No. 61/774,888, filed Mar. 8, 2013.
PCT/US2014/018150 filed Feb. 25, 2014.

\* cited by examiner

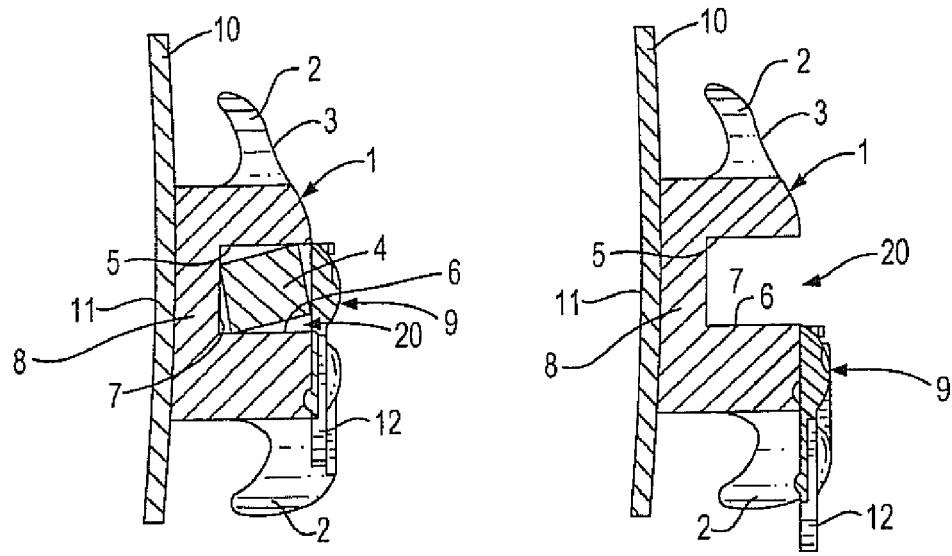
FIG. 1A
(Prior Art)
FIG. 1B
(Prior Art)
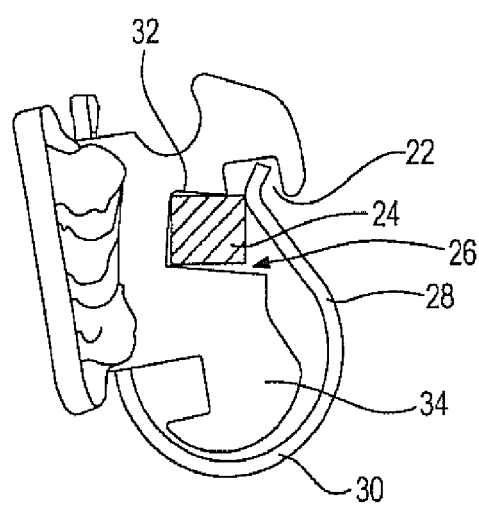
FIG. 2A
(Prior Art)

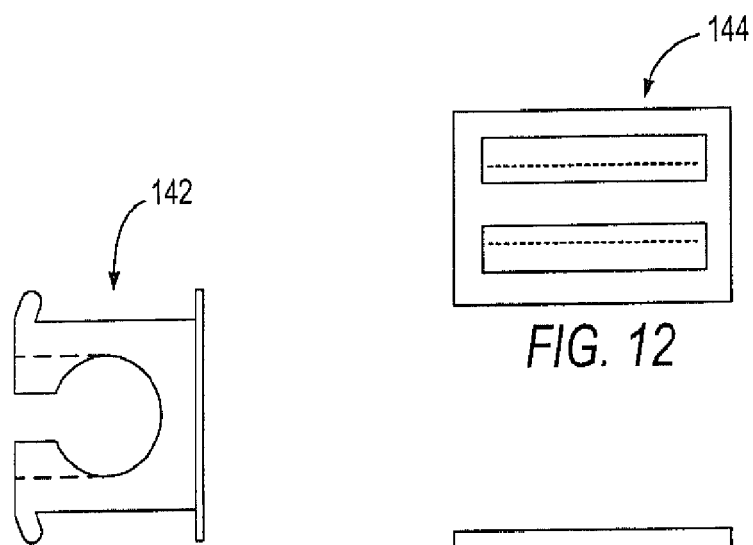
FIG. 11
FIG. 12
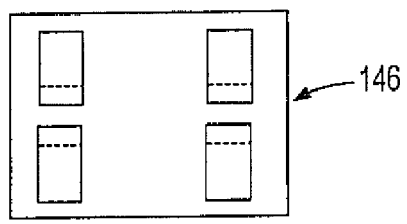
FIG. 13
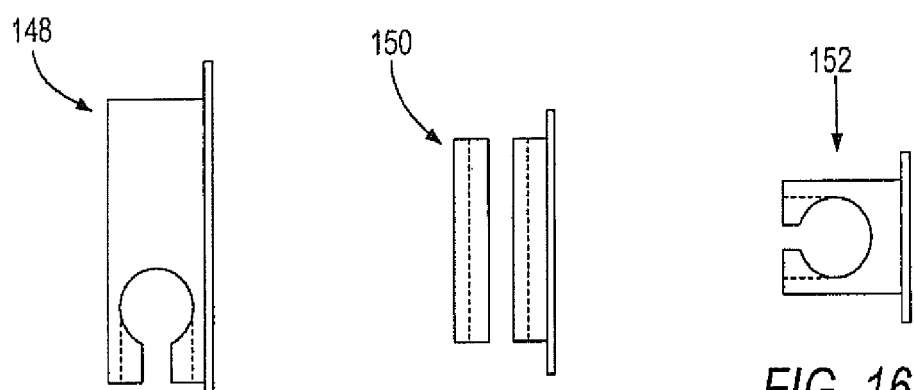
FIG. 14
FIG. 15
FIG. 16

STATIC SELF-LIGATING ORTHODONTIC BRACKET AND METHOD OF USING SAME

CROSS REFERENCE TO RELATED APPLICATIONS

This application relates to and claims priority as a 371 national-phase from PCT/us2014/018150 filed Feb. 25, 2014, the entire contents of which are incorporated herein by reference, which claims priority from US Prov. Ser. No. 61/774,888 filed Mar. 8, 2013, the entire contents of which are incorporated herein by reference.

BACKGROUND OF THE INVENTION

Field of the Invention

The present invention relates to orthodontic brackets and, specifically an orthodontic bracket wherein an orthodontic wire is held in an open channel or slot which receives an orthodontic wire without means of any type of applied ligature or any type of moving cover. More particularly, the present invention provides a static self-ligating orthodontic bracket.

Description of the Related Art

Orthodontic brackets are well known in prior art. Brackets are glued or cemented to the surface of teeth, or attached to metal bands cemented to a tooth and provide a means for a wire to be attached to a tooth. The wire applies force to the bracket which transmits it to the tooth to move the tooth in the desired manner. A bracket can also provide a slot for a wire to fit in and provide a guide to slide a tooth along a wire by means of force applied by various types of springs, elastics, or other devices to apply force to a bracket and subsequently transmitted to the tooth.

Existing bracket designs require a movable component of the bracket or an externally applied device known as a ligature to prevent the wire from becoming dislodged from the slot during orthodontic treatment. Another design known as a Begg bracket, uses a metal pin fitted into a slot to hold the wire in place. There are many variations on these types all of which require ligatures, pins, or movable components to secure an orthodontic wire into the bracket slot. Brackets which do not require an externally applied component such as a ligature to hold an orthodontic wire in place in the slot, are generally known as self ligating brackets.

Existing designs have a number of problems which hinder efficient orthodontic treatment. The movable component of self ligating brackets can become damaged through normal use in the oral environment, or through abuse by the patient. If the movable component is damaged the bracket may be rendered unusable and require replacement requiring additional clinical treatment time, discomfort to the patient, extension of treatment time, and additional expense. Ligatures require time to apply to each individual bracket, and in the case of esthetic brackets manufactured from transparent or tooth colored materials ligatures stained from various foods in the oral environment can be unsightly leading to patient dissatisfaction.

Orthodontic brackets represent a principal component of all corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that cause the teeth to move into correct positions. Traditional ligatures, such as small elastomeric O-rings or fine metal wires, are employed to retain the archwire within each bracket slot.

Due to difficulties encountered in applying an individual ligature to each bracket, self-ligating orthodontic brackets have been developed that eliminate the need for ligatures by relying on a movable portion or member, such as a latch or slide, for retaining the archwire within the bracket slot.

While self-ligating brackets have been generally successful, manufacturers of such brackets continually strive to improve the aesthetics associated with self-ligating brackets, the use and functionality of self-ligating brackets, and the costs and manufacturability of self-ligating brackets.

Orthodontic brackets attached to teeth engage an archwire that exerts forces upon them to move the teeth. Such brackets typically include an archwire slot for reception of the archwire. An archwire slot can have any desired cross-sectional configuration or size to match the size and shape requirements of the archwire, or archwires, that are to be engaged within the slot.

Orthodontic brackets today are typically bonded to a tooth with the archwire slot oriented parallel to the occlusal plane. However, the slot can also be angularly oriented across the bracket when desired.

Most brackets in use today include cleat extensions referred to as tie wings or lugs. they project upwardly and downwardly in pairs at the top and bottom of the installed bracket, respectively. These extensions conventionally permit the archwire to be held within the archwire slot of the bracket by means of a ligature, twisted wire (ligature) or an elastomer O-ring.

Numerous attempts have been made to design brackets that are self-ligating. For example, one such design discloses a slidable closure that engages the front of the archwire. The closure is recessed from the front or anterior surfaces of the disclosed bracket. The fact that such recessed sliding closures require the archwire also to be recessed within the archwire slot before the closure can be moved over the archwire makes it very difficult for the user to visually confirm that the archwire is properly seated within the archwire slot to facilitate closing of the slidable cover.

When using a conventional bracket and tying wires, proper seating of the archwire can be confirmed by visually noting that the anterior surface of the archwire is flush with the anterior surface of the bracket. It is desirable that a self-locking bracket provide similar visual reference capabilities to the user. This cannot be attained where no anterior surface of the bracket is available for visually referencing the position of an archwire within the archwire slot of the bracket.

A self-ligating bracket designed to mount an archwire flush with an anterior surface of an orthodontic bracket to facilitate visual positioning of the archwire during orthodontic treatment is also known. Such bracket disclosures utilize a ligating slide or closure that is permanently retained on the bracket during use, whether the closure is left in an open or closed condition, which guards against accidental release of the closure while the bracket is worn on a tooth.

Most importantly, the closure was designed to leave the usual tying extensions that protrude from the top and bottom of the bracket fully accessible to other orthodontic attachments for the application of torsional forces to the teeth. The exposed tying lugs remain always available for repositioning of the bracket and tooth by use of tying wires or other conventional attachment systems. One achievement of this bracket is the provision of a ligating slide within a bracket that maintains the normal features of protruding tie wings or lugs required by the profession.

The previous bracket embodiments also include a closure in the form of a ligating slide that can complete a continuous tube surrounding the archwire when the closure is in a closed position. This can be effectively achieved in a Siamese or twin bracket configuration without covering or interfering with projecting extensions on the bracket.

Another previous self-ligating orthodontic bracket discloses a locking slide member that is flat and guided by upright slots formed along both sides of the bracket and spanning the archwire slot. A resilient member or detent is provided to retain the slide member in either the open or closed position. No tie wings or lugs are included in the illustrated bracket forms.

Miniaturization of orthodontic brackets is extremely important today in view of the development of modern high-technology archwires. Patients desire small brackets to reduce the visual impact of the brackets while they are being worn. Orthodontists desire smaller brackets in order to more effectively use the biasing forces available in the high technology archwires, it being recognized that the force applied to a bracket by the archwire is decreased with increasing bracket spacing between teeth.

One drawback to miniaturization of the brackets shown in earlier patents is the fact that most of the embodiments wrap the cover over the sides of the bracket to engage grooves posterior to the archwire slot across the bracket. The width of the sliding cover therefore increases the total width of the bracket beyond that which is necessary due to the strength properties of the bracket itself. It is subject to tooth contact due to normal occlusion clearances in the mouth and subsequent failure or damage from the opposing dentition or food.

While the some known methods show a flat cover sliding within the lateral confines of a bracket, the guiding arrangement for the cover includes slots at both the superior and inferior sides of the archwire slot, thereby obscuring visual access to the critical corners of the archwire slots at the side edges of the bracket. Without this visual access being clear, one installing an archwire within a bracket cannot be certain as to proper seating of an archwire within the archwire slot before the slide cover is moved to a closed position. A wire not properly seated in the slot can cause damage to the cover mechanism and require replacement of the bracket interfering with treatment.

Referring to FIG. 1A, shown is a prior art self-ligating orthodontic bracket with the cover shown in a closed position with an archwire held within the bracket. Also, shown in FIG. 1B is the prior art self-ligating orthodontic bracket of FIG. 1A with the cover shown in the open position. The general concepts of the invention can best be understood from a study of the first embodiment of the assembled orthodontic bracket. This form of the bracket includes a movable closure separately shown in FIGS. 1A and 1B. The illustrated bracket, identified generally by the numeral 1, includes a pad 10 having a posterior surface 11 adapted to be bonded directly to a tooth. Pad 10 can be constructed integrally with the bracket 1 or can be a separate component added to it during assembly. The bracket 1 as shown in the drawings is a "Siamese" or pad 10. Tie wings 2 project anteriorly from the bracket 1. Each tie wing 2 two opposed extensions that project outwardly from bracket 1 between transversely spaced side surfaces.

At a minimum, each tie wing 2 includes an outer side surface. In addition, the tie wing configurations shown in the drawings further include inwardly facing side surfaces. The bracket 1 also includes first anterior surfaces 3 across the front of each first tie wing extension. The exposed anterior surfaces 3 extend across the full width of the bracket 1 and tie wing extensions.

Lower planar anterior surfaces lead to opposite sides of a transverse archwire slot generally designated by the numeral 20. The archwire slot 20 spans the full width of the bracket 1, where it opens across the bracket side surfaces. The space along archwire slot 20 between the tie wings 2 can be open, but is preferably enclosed by bracket walls joining the tie wings. This provides a supporting enclosure for an archwire 4 across the hill width of the bracket 1.

The archwire slot includes opposed and spaced side slot surfaces 5 and 6, plus an interconnecting anterior base 7. As can be seen in FIGS. 1A and 1B, the intersections of the side slot surfaces 5, 6 and anterior base 7 with the outer side surfaces of bracket 1 may be rounded or radiused. This provides a smooth edge for engagement by an archwire located within the archwire slot 20 and eliminates high stress and pressure on the archwire surfaces in contact with the ends of the archwire slot. It further facilitates motion between the bracket and archwire as tooth movement occurs in the mouth of a patient.

Side slot surface 5 forms a first transverse anterior corner with the archwire slot 20 where it intersects the anterior surface 3 of the first tie wing extensions. Side slot surface 6 similarly forms a second transverse anterior corner with the archwire slot 20 where it intersects the anterior surface of the second tie wing extensions. It is important to note that the second corner is continuous or coextensive across the full width of bracket 1 between the side surfaces. The anterior surface 3 across the first tie wing extension is free of any projections or closure guides. Thus, a clinician observing the installed bracket on a tooth has an unobstructed view of the open archwire slot 20 from its one side to guide him or her in proper bracket and archwire positioning procedures.

The slot surfaces 5, 6 and 7 are sized and configured in a manner complementary to the size and shape requirements of an archwire (or archwires) adapted to be received within the archwire slot. While the illustrated slot is rectangular and is designed specifically for reception of complementary rectangular archwires, it is to be understood that the slot can be configured as a cylinder or other cross-sectional shape in the manner presently known with respect to orthodontic bracket design. In use, the slot is partially or completely filled by the cross-sectional configuration of one or more archwires 4 located within it.

As shown, the tie wings 2 are integrally joined within the structure of bracket 1. An intermediate wall section 8 extending across the tie wings 2 in the bracket 1 includes first and second wall sections transversely joining the twin upright tie wings at positions superior and inferior to the archwire slot 20, respectively. Each of the first and second walls includes a surface spaced from one another and flush with the previously-described side surfaces 5, 6 along the archwire slot. The intermediate wall section 8 further includes a surface flush with the previously-described base slot surfaces 7 to provide a continuous archwire slot across the full width of the illustrated bracket 1.

The intermediate wall section 8 serves as a structural boundary surrounding three sides of the archwire slot 20 in the space located between the tie wings 2. In combination with the closed ligating slide 9, it forms a continuous tube across the width of the bracket for reception and capture of an archwire.

A closure complementary to the archwire slot is also provided on the illustrated bracket 1. It takes the form of a ligating slide 9 that is generally planar. The ligating slide movably engages the anterior surfaces of the second tie wing extensions. According to this disclosure, the ligating slide 9 is supported for motion relative to bracket 1 only along the second extensions of the tie wings 2. The anterior portion of second extension of each tie wing 2 includes a guide 9 having an upright inwardly facing guide slot 12. Each guide slot 12 is located anteriorly from the second anterior surfaces.

When the ligating slide 9 is in its open position, the intersection formed between its posterior surface and its open edge is juxtaposed to the corner of side slot surface 6. In this condition, the contiguous corners of the side slot surface 6 and slide 9 provide uninterrupted access to the interior of archwire slot 20. As can be seen in FIGS. 1A and 1B, the cantilevered support for the ligating slide 9 assures a user of an unobstructed oblique view of the archwire slot 20 when looking toward the mouth of one wearing the brackets. This is true whether the bracket is mounted on a lower tooth or an upper tooth. A clinician can therefore readily observe the position of an archwire 4 relative to the boundaries of the archwire slot 20 before closing the ligating slide 9. To assure full width visual and physical access to the archwire slot 20, the open edge of the ligating slide 9 is preferably flush with the inferior side slot surface 6 when the ligating slide 9 is in its retracted or open position.

The anterior surface of ligating slide 9 has a pair of protruding stops at its sides and adjacent to its open edge. The stops are designed to abut the ends of the walls so as to limit the opening movement of the ligating slide 9 relative to the bracket 1. Ligating slide 9 is essentially planar and rigid. However, it is desirable to reinforce its strength by the addition of one or more transverse enlarged ribs.

Looking next at FIGS. 2A-C, shown is another known self ligating orthodontic bracket. FIG. 2A shows a view from the mesial of a prior art bracket 34, shown with a rectangular cross section arch wire 24 of maximum transverse cross section dimensions in the arch wire slot 26. As shown, in order to protect the spring member labial arm portion 28 against excessive labial movement under the action of the arch wire, the prior art bracket 34 has been provided in the arch wire slot gingival surface with a slot 22 extending from the mesial surface to the distal surface and opening to both of those surfaces, into which slot the end of the spring member labial arm portion 28 can extend when in the slot closed position. The slot 22 must be of substantial labial lingual dimension to permit ready insertion of the spring member 30 end therein while the arch wire 24 is displaced out of the slot 26, and to permit the spring member 30 to still engage the arch wire 24 when it is fully inserted in the slot 26. As seen in FIG. 2A, the most usual result is that the presence of the slot reduces the labial lingual dimension of the arch wire slot gingival face 32 to substantially less than the corresponding dimension of the arch wire gingival surface, particularly when the arch wire is of the largest transverse cross section dimensions that can be accommodated in the slot, with the attendant disadvantages discussed above.

FIG. 2B shows a perspective view from the mesial and labial of a prior art bracket, showing in broken lines the ligating latch spring member in slot closed position, while FIG. 2C shows a cross section in a gingival occlusal plane through the prior art bracket of FIG. 2B, showing in solid lines an arch wire of rectangular transverse cross section in the arch wire slot and the corresponding position of the spring member labial portion, showing in broken lines an arch wire of circular transverse cross section in the arch wire slot and the corresponding position of the spring member labial portion, and illustrating the manner in which an opening tool is used in conjunction therewith.

In the brackets 34 of the invention the gingival surface 32 is instead provided with a mesially distally extending retaining recess 36 of smaller mesial distal width than the gingival surface, so that it is closed at its mesial and distal ends and thereby provides labial lingual extending gingival rail surfaces 38 (colloquially referred to as torquing rails) at the closed mesial and distal ends, these rail surfaces being engagable by the arch wire 24 gingival surface over the full labial lingual extent thereof for maximum application of torque moment from the arch wire 24 to the bracket 34. In the embodiments of FIGS. 2A-C the width dimension of the entire spring member 30 in the mesial distal direction is smaller than that of the slot gingival surface 32, and in particular sufficiently smaller than the mesial distal width of the retaining recess 36 that the free end part of the labial portion can be inserted into the recess when the spring member 30 is in the slot closed position, thereby protecting it against excessive labial movement. The labial lingual dimension of the retainer recess 36 is such that the spring member 30 is able to engage the smallest cross-section arch wire 24 with which the bracket 34 is to be used, and is also able to accommodate the largest cross section wire that is to be used with a small amount of clearance between it and the wire when mesial distal movement along the arch wire is required. The maximum extent of the labial movement that is permitted by the recess 36 is well within the amount that would result in over-stressing and damage to the spring retainer member 30, even when the member is of stainless steel and not of one of the shape memory metal alloys.

Accordingly, there is a need for an improved orthodontic bracket wherein an orthodontic wire is held in an open channel or slot which receives an orthodontic wire without means of any type of applied ligature or any type of moving cover. More particularly, there is a need for an improved static self-ligating orthodontic bracket.

SUMMARY OF THE INVENTION

The present invention relates to orthodontic brackets and, specifically an orthodontic bracket wherein an orthodontic wire is held in an open channel or slot which receives an orthodontic wire without means of any type of applied ligature or any type of moving cover. More particularly, the present invention provides a static self-ligating orthodontic bracket. In accordance with one aspect of this invention, the orthodontic bracket of the present invention consists of a slot designed in such a manner that an orthodontic wire will be secured in place in the slot by means of a rotational movement about the long axis of the wire after insertion into the slot.

The slot will generally have in interior width greater than the width at the entrance to the slot. Orthodontic brackets known generically as Edgewise brackets usually have one of two slot sizes (i.e., 0.018 inches (in)×0.025 in or 0.022 in×0.028 in) with parallel sides.

Orthodontic wires are made with numerous cross sectional geometries. The wire used with this invention will be required to have a cross section that is not circular. Most preferably the wire has a narrow aspect and a wide aspect in order that it may be twisted on its long axis in order to present its narrowest dimension while being inserted into the slot of the bracket. The wire used in accordance with this invention is formed in a shape so that after insertion into the bracket slot the portion of the wire facing the slot is wider than the slot that keeps the wire from becoming dislodged from the bracket slot.

The slot geometry can be designed in such a manner that the wire will apply force to the bracket and cause tooth movement after the wire is placed in the bracket slot. The bracket slot can be any of the following shapes: round; oval; square; diamond; irregular; or any shape designed to provide a place for the wire to lodge and transmit force to the teeth and cause intended tooth movement.

Wires to be used in accordance with the present invention may be manufactured using digital data indicating the bracket position on the teeth and the position of the teeth in the dental arches and the orientation of the dental arches to each other and to other bodily structures of the mouth region. This digital data may be captured by means of intra oral digital scanners used in the mouth, as well as scanning devices to scan plaster dental casts or dental impressions. Digital data may also be captured by means of digital radiography, cone beam or volumetric tomography being commonly used, or via use of a digital positioning wand and a three-dimensional recorder. The digital data may also be used to manufacture wires compatible with the present invention, which are generally manufactured with a computer controlled robotic machine. Generally, the wire in accordance with the invention may have any of the following cross-sectional configurations: oval; rectangular; irregular; or any complex shape with one aspect narrower then the slot entrance.

It is a principal aspect of the present invention to provide a new self-ligating orthodontic bracket which requires no moving components or externally applied ligatures to hold the wire in place.

It is another aspect of the present invention to provide a new family of self-ligating orthodontic brackets, such brackets depending on computer designed and robot manufactured wires. Common scanners for producing brackets in accordance with the invention may include the IOC scanner made by Cadent, Inc., a division of Align Technology, Inc., 2560 Orchard Parkway, San Jose, Calif. 95131 USA, the Trios scanner made by 3Shape A/S. Holmens Kanal 7, 1060 Copenhagen K, Denmark, and the D900 Lab Scanner made by 3Shape A/S. Holmens Kanal 7, 1060 Copenhagen K, Denmark. Other scanners capable of producing these brackets may also exist. Also, known arch wire manufacturers capable of making wires compatible with the static self-ligating orthodontic bracket according to the invention include Orametrix, Inc., 2350 Campbell Creek BLVD, STE 400, Richardson, Tex. 75082 USA, and Unitek, 3M Unitek, Orthodontic Products, 2724 South Peck Road, Monrovia, Calif. 91016 USA. Of course, other companies may also exist and are known to those of skill in the art.

It is yet another aspect of the present invention to provide new self-ligating orthodontic bracket provided with any of a variety of arch wire slot geometrical configurations, such as oval, round, square, irregular, kidney-shaped, etc., to secure the arch wire therein.

It is still another aspect of the present invention to provide new self-ligating orthodontic brackets for use with pre-tensioned arch wires, the brackets having slot for retaining the arch wires therein during use, the slots having pins, hooks or other restraining means to hold the arch wire in place by restraining rotation of the arch wire while positioned in the slot.

Still another aspect of the present invention is to provide a one-piece self-ligating slotted orthodontic bracket which may have a low profile for comfort, and which is constructed to have tie hooks, or other auxiliary holes, slots, or other protuberances, etc. to allow the exertion of additional force on the arch wire through external means.

In accordance with the invention there is provided a static self-ligating orthodontic bracket for coupling a pre-tensioned arch wire with a tooth, wherein the bracket comprises a bracket body configured to be mounted to a tooth, an arch wire slot configured for receiving a pre-tensioned arch wire therein, the arch wire slot configured with a plurality of protruding stops on an interior wall surface thereof, the stops spaced apart from one another, and a slot opening for receiving the arch wire into the arch wire slot, the opening having a width less than a diameter of the arch wire slot, wherein the arch wire is configured with a non-spherical cross-section. Preferably, the arch wire has a rectangular cross-sectional configuration, but its cross-section may also be of other configurations such as oval, oblong, egg-shaped, kidney-shaped, etc. Preferably, the arch wire slot has a round cross-sectional configuration but the arch wire slot may also have a cross-sectional configuration that is oval, rectangular, oblong, egg-shaped, irregular and kidney-shaped. The bracket body is preferably made from metal, ceramic or polymer, but may be made of other known, safe materials for use in orthodontics, or may be a composite of different suitable materials. Optionally, the bracket body may comprise a tie wing positioned on each of an upper end and a lower end thereof. The slot opening may be configured to open in a gingival, facial or labial orientation, or any desired orientation.

Also in accordance with the invention there is provided a method comprising the steps of fastening a bracket body to a surface of a tooth, selecting an appropriate pre-tensioned arch wire for application to a bracket, applying force to straighten said pre-tensioned arch wire, orienting said straightened arch wire for insertion into an arch wire slot of said bracket body, inserting said straightened arch wire into said arch wire slot of said bracket body, and applying a rotational moment to said arch wire while said arch wire is within said slot to lock said arch wire in place within said arch wire slot of said bracket body.

The wire also applies force in any desired direction or a moment (force) about any desired axis in order to produce a force in a desired vector to apply a desired force to a tooth or series of teeth.

The above and other aspects, features and advantages of the present invention will become apparent from the following description read in conjunction with the accompanying drawings, in which like reference numerals designate the same elements.

BRIEF DESCRIPTION OF THE DRAWINGS

A further understanding of the present invention can be obtained by reference to a preferred embodiment set forth in the illustrations of the accompanying drawings. Although the illustrated preferred embodiment is merely exemplary of methods, structures and compositions for carrying out the present invention, both the organization and method of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which:

FIG. 1A depicts a prior art self-ligating orthodontic bracket with the cover shown in a closed position having an arch wire held within the bracket.

FIG. 1B shows the prior art self-ligating orthodontic bracket shown in FIG. 1A with the cover shown in an open position.

FIG. 2A depicts a mesial view of a prior art self-ligating orthodontic bracket shown with a rectangular cross-section arch wire of maximum transverse cross-section dimensions in the arch wire slot.

FIG. 3A shows the arch wire prior to placement in the arch wire slot of the bracket. FIG. 3B shows the arch wire twisted about its long axis prior to insertion in the slot of the bracket. FIG. 3C shows the insertion of the arch wire into the slot of the bracket. FIG. 3D shows the arch wire being locked in place by applying a counterclockwise moment to the arch wire or bracket. FIG. 3E shows the arch wire being locked in place by applying a clockwise moment to the arch wire or bracket. FIG. 3F shows the arch wire locked in place in the bracket slot and in a passive state with no force applied.

FIG. 11 shows a side view of a preferred embodiment of the static self-ligating orthodontic bracket in accordance with the present invention, with the arch wire opening in a labial orientation, with the bracket further including tie wings for use with ligatures (i.e., rubber bands, etc.).

FIG. 12 shows a front plan view of a preferred embodiment of a single wing static self-ligating orthodontic bracket in accordance with the present invention illustrating the arch wire opening in a labial orientation and its difference in width from the diameter of the arch wire slot within the bracket body (indicated with dashed lines).

FIG. 13 shows a front plan view of a preferred embodiment of a double or twin wing static self-ligating orthodontic bracket in accordance with the present invention illustrating the arch wire opening in a labial orientation and its difference in width from the diameter of the arch wire slot within the bracket body (indicated with dashed lines).

FIG. 14 shows a side view of a preferred embodiment of a static self-ligating orthodontic bracket in accordance with the present invention illustrating the arch wire opening in a gingival orientation and its difference in width from the diameter of the arch wire slot within the bracket body (indicated with dashed lines).

FIG. 15 shows a top plan view of a preferred embodiment of a static self-ligating orthodontic bracket in accordance with the present invention illustrating the arch wire opening in a facial orientation and its difference in width from the diameter of the arch wire slot within the bracket body (indicated with dashed lines).

FIG. 16 shows a side view of a preferred embodiment of the static self-ligating orthodontic bracket in accordance with the present invention, with the arch wire opening in a labial orientation.

DETAILED DESCRIPTION OF THE PREFERRED EMBODIMENTS

Figure 2B:
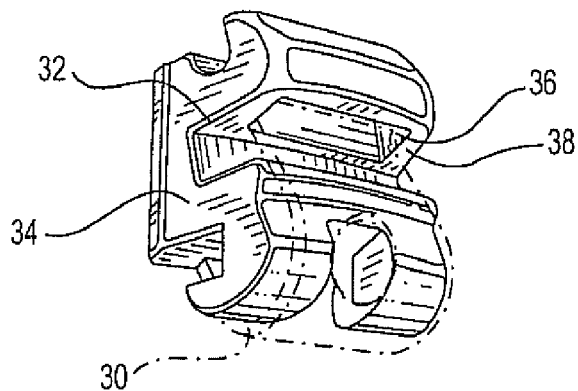
FIG. 2B depicts a perspective mesial and labial view of a prior art self-ligating orthodontic bracket showing in broken lines the ligating latch spring member in a closed slot position.
Figure 2C:
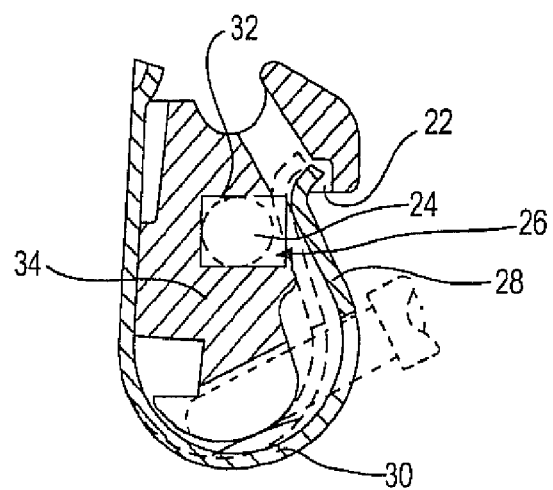
FIG. 2C shows a cross-sectional view in a gingival occlusal plane of the prior art bracket shown in FIG. 2B, depicting in solid lines an arch wire of rectangular transverse cross-section in the arch wire slot and the corresponding position of the spring member labial portion, showing in broken lines an arch wire of circular transverse cross-section in the arch wire slot and the corresponding position of the spring member labial portion, and illustrating the manner in which an opening tool is used in conjunction therewith.

As required, a detailed illustrative embodiment of the present invention is disclosed herein. However, techniques, systems, compositions and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

Reference will now be made in detail to several embodiments of the invention that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, below, etc., or motional terms, such as forward, back, sideways, transverse, etc. may be used with respect to the drawings. These and similar directional terms should not be construed to limit the scope of the invention in any manner.

It will be noted that self ligating brackets come in two general types, active or passive. An active bracket is defined as having a spring loaded member maintaining a continuous force on the inserted wire when the movable self ligating member is activated. A passive self ligating bracket has a door or latch which seals the slot closed and provides a 'tub/tube' for the wire to lie in. Some brackets are both active and passive depending upon how the movable member is inserted or closed. Therefore, this invention will be understood by those of skill in the art as being either active or passive depending upon the bends placed in the wire during manufacture, and not necessarily restricted in either way. If a wire maintains a constant pressure after insertion it is active and if the wire only twists on its axis enough to lock into position but not apply force to the sides of the slot it is passive. The bracket can change from active to passive because the tooth generally moves away from the applied force and may move enough so that the wire no longer applies force to the bracket. Once applied force drops to less than that which is necessary biologically to move teeth, the tooth will stop moving and the wire will be held in place by the slot design.

Figure 3A:
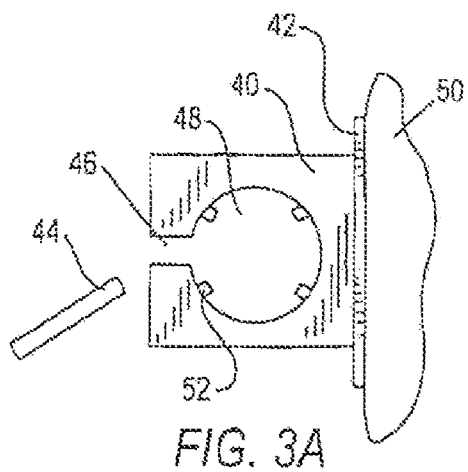
FIGS. 3A-F illustrate a cross-sectional view of a preferred embodiment of the static self-ligating orthodontic bracket in accordance with the present invention, and the insertion and restraint of a pre-tensioned arch wire therein, the arch wire having a generally rectangular cross-sectional configuration, and the arch wire slot of the bracket having a generally round shape or configuration. For the sake of clarity, the slot is shown here as round with four (4) stops, however, it should be noted that any shape slot may be used so long as its diameter is larger inside than at the entrance, and some geometric means of locking the arch wire in place is provided. More specifically.
Figure 3B:
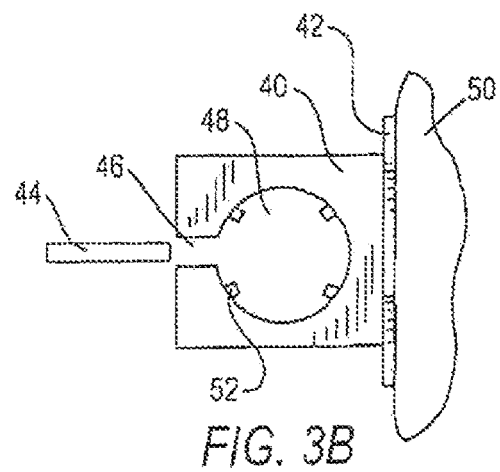
Figure 3C:
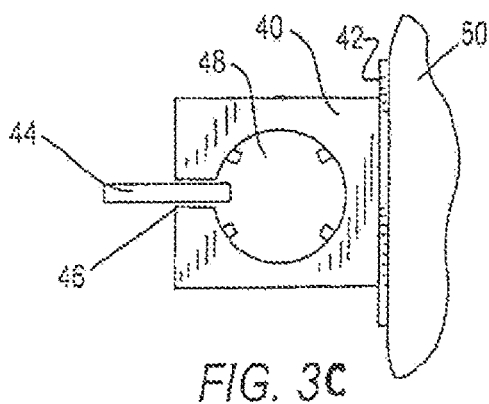
Figure 3D:
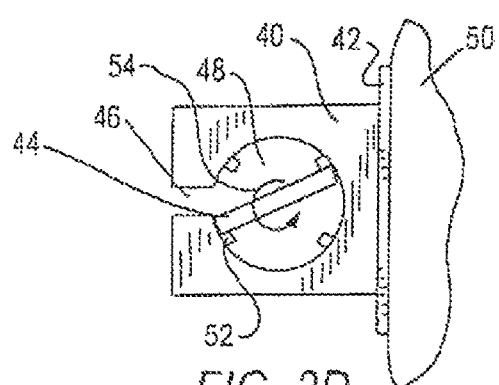
Figure 3E:
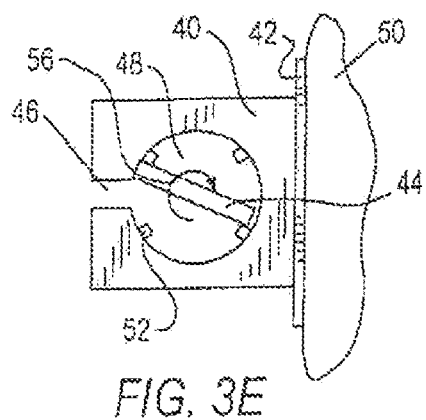
Figure 3F:
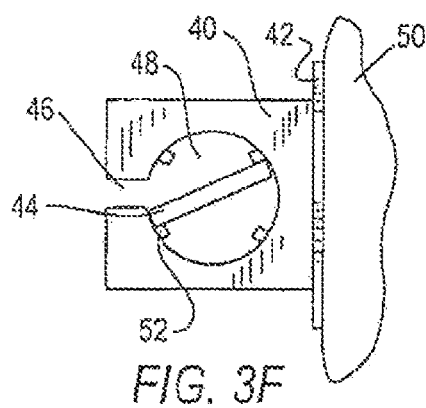

Referring first to FIGS. 3A-3F, illustrated are cross-sectional views of the preferred embodiment of the static self-ligating orthodontic bracket in accordance with the present invention, further showing the insertion and restraint of a pre-tensioned arch wire 44 therein. As shown, the arch wire 44 has a generally rectangular cross-sectional configuration, and the arch wire slot 48 of the bracket having a generally round shape or configuration. For the sake of clarity, the arch wire slot 48 is shown here as round with four (4) stops 52, however, it should be noted that any shape slot 48 may be used so long as its diameter is larger inside than at the entrance, and some geometric means of locking the arch wire 44 in place is provided. More specifically, FIG. 3A shows the arch wire 44 prior to placement in the arch wire slot 48 of the bracket body 40. FIG. 3B shows the arch wire 44 twisted about its long axis prior to insertion in the slot 48 of the bracket 40. FIG. 3C shows the insertion of the arch wire 44 into the slot 48 of the bracket 40. FIG. 3D shows the arch wire 44 being locked in place by applying a counter-clockwise moment to the arch wire 44 or bracket 40. FIG. 3E shows the arch wire 44 being locked in place by applying a clockwise moment to the arch wire 44 or bracket 40. FIG. 3F shows the arch wire 44 locked in place in the bracket slot 48 and in a passive state with no force applied. Importantly, the arch wire 44 must not be twisted to the point where permanent deformation takes place during insertion or removal. If this occurs, then the arch wire 44 will be unable to exert the necessary force within bracket 40 to effectuate the purpose of the system.

In conventional orthodontic treatment arch wires vary in dimension as well as spring temper and material in order to provide varying forces to teeth. With this bracket, all wires must be the same dimension and designed to work with a particular bracket so they will lock into place. Varying force is produced by various permanent bends, loops, and twists about the long axis of the wire, various types of materials (i.e., metallic and non metallic or composites of varying materials), or various stiffness of the wires.

The slot can be oriented in all three planes of space or any variation depending on the design of the bracket. It can open to the gingival, facial, or occlusal. The bracket geometry, not the shape of the bracket or the position of the slot or slots in the bracket is the invention here. The bracket can have various other holes, slots, hooks as desired and dictated by the needs of orthodontic technique. The bracket can be made of metal, ceramic, polymer, or any other suitable material. Brackets can be positioned on the labial or lingual surfaces of the tooth. The wire can be any size or shape as long as it will lock into the bracket slot after insertion due to twisting about its long axis.

FIGS. 3A-F also illustrate the application of the bracket and arch wire system to the teeth of a patient in accordance with the invention. That is, during use, a practitioner or user first fastens or otherwise bonds a bracket body 40 to the surface of each of the patient's teeth. Optionally, a pad 42 or other bonding material or device may be employed to secure the bracket 40 to the tooth 50. The practitioner then selects the appropriate pre-tensioned arch wire 44 configuration for the particular patient's needs. Once all of the bracket bodies 40 have been attached and are ready to receive the arch wire 44, the practitioner applies a force to straighten out the pre-tensioned arch wire 44 prior to insertion into the bracket body 40. The practitioner then orients the straightened pre-tensioned arch wire 44 by twisting or rotating it about its long axis such that its narrow width is oriented for insertion into arch wire slot of a first bracket body. The rotated straightened pre-tensioned arch wire 44 is then inserted into arch wire slot 48 of a first bracket body 40 through the opening 46 therein.

Once the arch wire 44 is fully inserted into arch wire slot 48 the practitioner applies a clockwise or counterclockwise moment to the arch wire 44 to lock the arch wire 44 in place within the arch wire slot 48 of the bracket body 40. To complete the process, the practitioner would then repeat the above steps above for each of the remaining bracket bodies 40 on each of patient's teeth. Finally, any excess arch wire 44 would be cut and discarded. Once finished, each bracket body 40 has arch wire 44 locked in position within the arch wire slots 48.

Figure 4A:
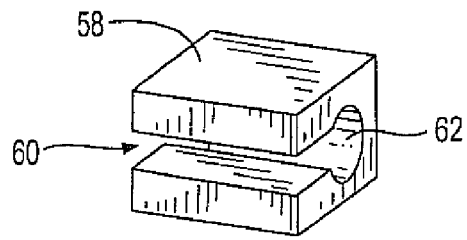
FIGS. 4A-B show perspective views of a single wing self-ligating orthodontic bracket in accordance with the invention illustrating the bracket opening in a labial configuration.
Figure 4B:
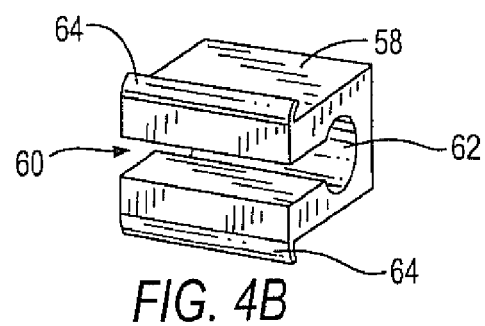

Turning next to FIGS. 4A-B, 5A-B and 6A-B, shown are perspective views of alternative embodiments of self-ligating orthodontic brackets in accordance with the invention. In particular, FIGS. 4A-B show a single wing self-ligating orthodontic bracket 58 in accordance with the invention illustrating the bracket 58 opening in a labial configuration. As shown, bracket 58 may comprise opening 60 and arch wire slot 62. Preferably, as shown, arch wire slot 62 has a round configuration but is not so limited. Also, preferably, the width of opening 60 is dimensionally smaller or less than a diameter of arch wire slot 62. Such a configuration will facilitate the insertion into and restraint within slot 70 of an arch wire. Optionally, the bracket 58 may include tie wings 64 for the inclusion or use of rubber bands or other ligatures during use of the orthodontic system.

Figure 5A:
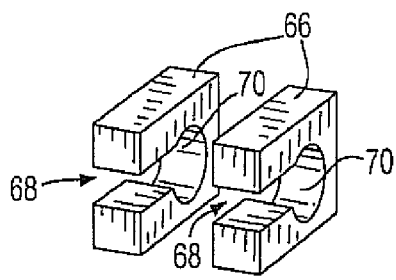
FIGS. 5A-B show perspective views of a double or twin wing self-ligating orthodontic bracket in accordance with the invention illustrating the bracket opening in a labial configuration.
Figure 5B:
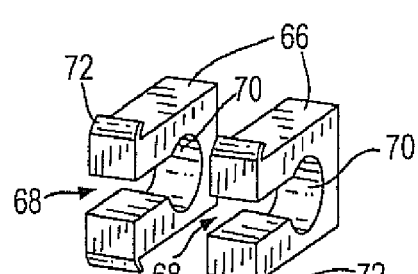

The brackets shown in FIGS. 4A-B comprise a single wing embodiment. That is, on each tooth only a single bracket component is applied. However, in accordance with the invention, double wing or twin wing brackets 66 may be employed, as seen in FIGS. 5A-B. As shown, brackets 66 may comprise openings 68 and arch wire slots 70. Preferably, as shown here and as described above regarding FIGS. 4A-B, arch wire slots 70 have round configurations but they are not so limited. Also, preferably, the widths of openings 68 are dimensionally smaller or less than the diameter of arch wire slots 70. Such a configuration is designed to facilitate the insertion into and restraint within slot 62 of an arch wire. Optionally, the brackets 66 may include tie wings 72 for the inclusion or use of rubber bands or other ligatures during use of the orthodontic system.

Figure 6A:
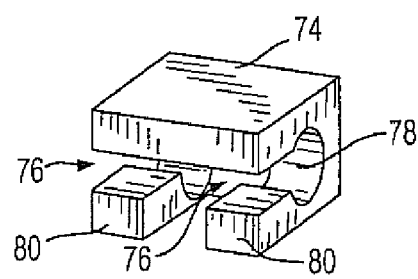
FIGS. 6A-B show perspective views of a single-double combined wing self-ligating orthodontic bracket in accordance with the invention illustrating the bracket opening in a labial configuration.
Figure 6B:
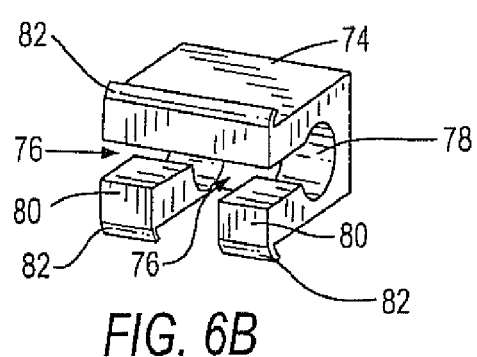

In accordance with yet another alternative embodiment of a bracket according to the invention, a single-double combined wing bracket 74 may be employed, as seen in FIGS. 6A-B. As shown, brackets 74 may comprise openings 76 and arch wire slot 78 formed by a single upper portion and a double lower portion 80. Preferably, as shown here and as described above regarding FIGS. 4A-B, arch wire slot 78 have round configurations but they are not so limited. Also, preferably, the width of opening 76 is dimensionally smaller or less than the diameter of arch wire slot 78. Such a configuration is designed to facilitate the insertion into and restraint within slot 78 of an arch wire. Optionally, the brackets 74 may include tie wings 82 for the inclusion or use of rubber bands or other ligatures during use of the orthodontic system.

Figure 7A:
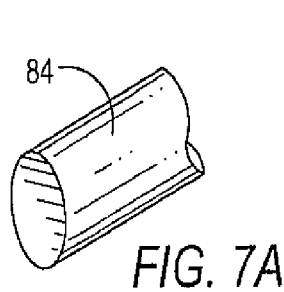
FIGS. 7A-C show partial cut-away perspective cross-sectional views of pre-tensioned arch wires for use in combination with a self-ligating orthodontic bracket according to the invention, with FIG. 7A showing an oval cross-section, FIG. 7B showing an irregular or kidney-shaped cross-section, and FIG. 7C showing a rectangular cross-section.
Figure 7B:
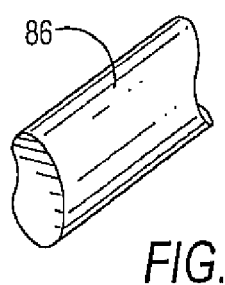
Figure 7C:
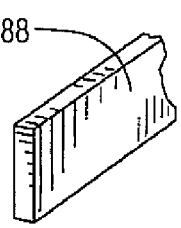

The arch wires for use in accordance with the invention may take any of a number of shapes and forms, and be made from a number of known materials, as discussed herein. As shown in FIGS. 7A-C, which depict partial cut-away perspective cross-sectional views of pre-tensioned arch wires for use in combination with a self-ligating orthodontic bracket according to the invention, the arch wires may have an oval cross-section 84 (FIG. 7A), an irregular or kidney-shaped cross-section 86 (FIG. 7B), or a rectangular cross-section 88 (FIG. 7C). It is important to note that the arch wires 84, 86, 88 for use in accordance with the invention must have a cross-section configured with a long and a short dimension that are substantially perpendicular with one another. Such a configuration is designed to facilitate the insertion and restraint of the arch wire within the bracket during use.

Figure 8A:
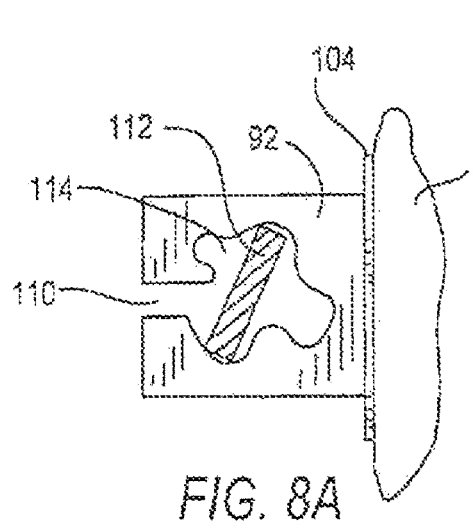
FIGS. 8A-C show side cross-sectional views of self-ligating orthodontic brackets according to alternative embodiments of the invention illustrating various cross-sections of the openings for placement of the pre-tensioned arch wire, with FIG. 8A showing an irregular opening or slot configuration, FIG. 8B showing a kidney-shaped opening or slot configuration, and FIG. 8C showing a square or diamond-shaped opening or slot configuration.
Figure 8B:
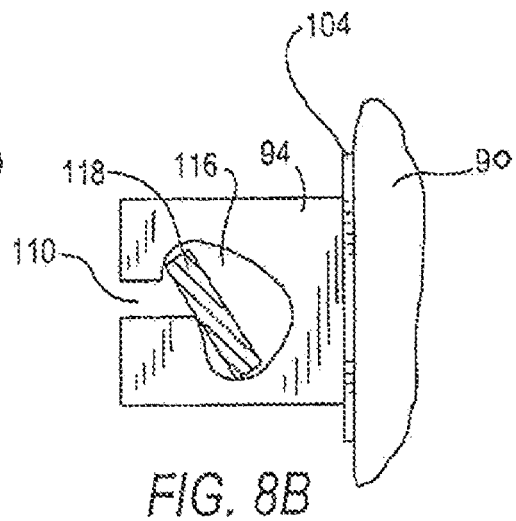
Figure 8C:
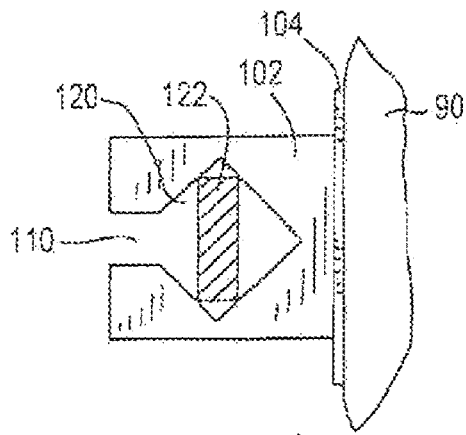

Turning next to FIGS. 8A-C, shown are side cross-sectional views of self-ligating orthodontic brackets 92, 94, 102 according to alternative embodiments of the invention illustrating various cross-sections of the slots 114, 116, 120 for placement of the pre-tensioned arch wire. As seen in FIG. 8A, an irregular opening or slot configuration 114 may be employed such that arch wire 112 may be restrained therein after insertion through opening 110, without the use of additional stops or internal restraints. As seen in FIG. 8B, a kidney-shaped opening or slot configuration 116 may be employed such that arch wire 118 may be restrained therein after insertion through opening 110, also without the use of additional stops or internal restraints. Lastly, as seen in FIG. 8C, a square or diamond-shaped opening or slot configuration 120 may be employed such that arch wire 122 may be restrained therein after insertion through opening 110, also without the use of additional stops or internal restraints.

Figure 9A:
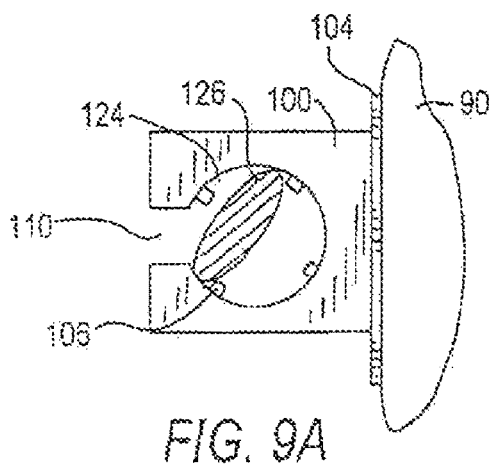
FIGS. 9A-C show side cross-sectional views of self-ligating orthodontic brackets according to other alternative embodiments of the invention illustrating the positioning of pre-tensioned arch wires therein, with the arch wires having different cross-sections.
Figure 9B:
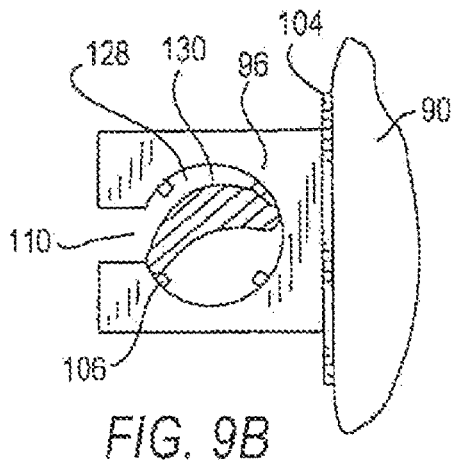
Figure 9C:
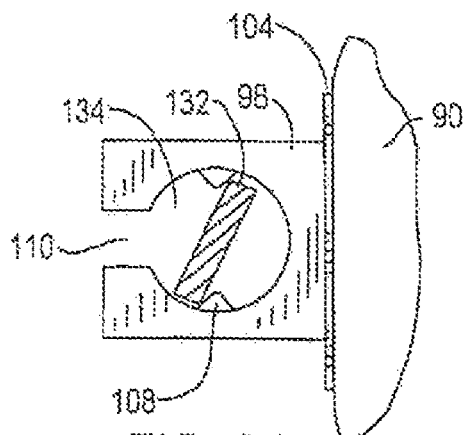

Alternatively, arch wires having different cross-sections may be used in accordance with the invention, in particular when using a bracket having a round arch wire slot 124, 128, 134, as shown in FIGS. 9A-C, which depict side cross-sectional views of self-ligating orthodontic brackets 100, 96, 98 according to other alternative embodiments of the invention illustrating the positioning of pre-tensioned arch wires 126, 130, 132 therein, with the arch wires 126, 130, 132 having different cross-sections (i.e., oval 126, kidney-shaped 130, and rectangular 132). As shown, stops 106, 108 are preferably employed on the internal surface of slots 124, 128, 134 to restrain the arch wire 126, 130, 132 after insertion through opening 110. Optionally, as shown in FIGS. 8A-C and 9A-C, a pad 104 or other bonding material or device may be employed to secure the bracket 92, 94, 100, 102, 98 to the tooth 90.

Figure 10:
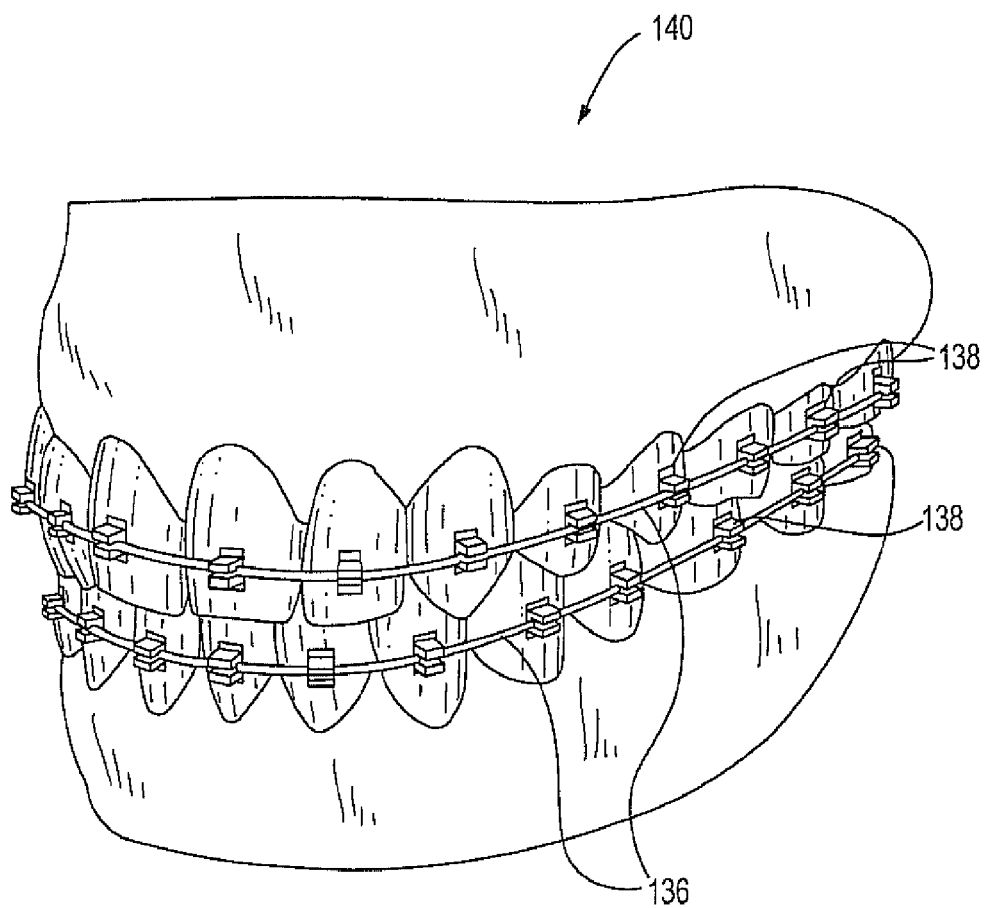
FIG. 10 shows a perspective view of a plurality of the brackets shown in FIGS. 3A-F and FIG. 4A on a set of teeth with two pre-tensioned arch wires.

Referring next to FIG. 10, shown is a perspective view of a plurality of the brackets 138 shown in FIGS. 3A-F and 4A on a set of teeth with two arch wires 136. As shown, the system 140 includes a plurality of brackets 138 secured on a patient's teeth. In many prior art bracket systems, different types of brackets (different shape, different slot prescription and different anatomy) were secured on different teeth. However, in a preferred embodiment of system 140, all of the teeth to be corrected include a bracket 138 secured thereon (e.g., molars, premolars, canines, lateral incisors and central incisors, etc.). It will be understood that the brackets 138 may be different sizes, e.g., height or width or thickness, but that each of the brackets 138 have the same design. Since the slots are round (and not rectangular), arch wires 136 can be threaded through all of the brackets 138 starting at the midline and continuing posteriorly. In other words, the arch wires 136 can be positioned by placing a wire portion at the midline into the mesial openings of the slots of the central incisor brackets 138 (positioning for one bracket), and then repeatedly placing (orientating and twisting as required for alignment with each respective slot) through the other brackets 138. It will be understood, that a user will gap one end of an arch wire (in a tool or by finger) orient a portion to fit within a first slot, then transition to the next arch wire location proximate the second slot, conduct an orientation and insertion for that second slot, and repeat for all the required brackets. Thus, as the arch wire may adapt and twist during the insertion process, the user orients proximate each bracket as required for insertion trough the slot. Therefore, after all of the brackets 138 have been linked by the arch wire, the arch wires 136 extend continuously through all of the brackets 138 of the system 140 and extend from the molar(s) on one side of the arch through the slot associated with each intervening tooth and to the molar(s) on the other or opposing side. In an alternative embodiment, the arch wires may be segmented.

It will be understood that the use of a second arch wire may provide for more rotational control and efficiency as it aids the first arch wire in straightening the teeth as both arch wires 136 regain their initial shape via the shape memory properties inherent in the materials used. In a preferred embodiment, the arch wires 136 are made of nickel titanium. However, this is not a limitation on the present invention and other shape memory alloys or materials may be used. It will be understood that the system 140 can be used with one or two arch wires.

Threading the arch wire 136 through the slots increases operator efficiency, decreases the chance for patient/operator injury with instruments and increases patient comfort because the forces related to ligating traditional brackets are unneeded. At adjustment visits, the wires can be removed the same way that they are inserted (threaded) which also provides for more efficiency, less chance of injury and less discomfort for the patient.

It will be understood by those skilled in the art, that in many cases or treatments of a patient (e.g., in a case where the teeth are crooked and no spaces need to be closed) nothing other than the friction of the superelastic arch wires 136 within the slots is necessary to hold the arch wires 136 in place. However, some cases may require further aid in moving the teeth. This may be accomplished through the use of tie wings and the spaces defined between the tie wings and the base. The wings can be used in a number of different situations. For example, when a patient needs space between teeth closed, the treating doctor may need to use some type of elastic, such as what is called a power chain. All components that are used to retain the arch wire 136 on or in the bracket 138, including ligatures ties, power chains, clips, elastomeric rings and the like. It will be understood by those skilled in the art that the tie wings are used to retain the power chain or elastic on the bracket 138 and over the arch wire 136. This allows the power chain or elastic to exert forces that consolidate and pull the teeth towards one other or in some other desired direction.

Turning now to FIG. 11, shown is a side view of a preferred embodiment of the static self-ligating orthodontic bracket 142 in accordance with the present invention, with the arch wire opening in a labial orientation, with the bracket further including tie wings for use with ligatures (i.e., rubber bands, etc.). FIG. 12 shows a front plan view of a preferred embodiment of a single wing static self-ligating orthodontic bracket 144 in accordance with the present invention illustrating the arch wire opening in a labial orientation and its difference in width from the diameter of the arch wire slot within the bracket body (indicated with dashed lines). FIG. 13 shows a front plan view of a preferred embodiment of a double or twin wing static self-ligating orthodontic bracket 146 in accordance with the present invention illustrating the arch wire opening in a labial orientation and its difference in width from the diameter of the arch wire slot within the bracket body (indicated with dashed lines). FIG. 14 shows a side view of a preferred embodiment of a static self-ligating orthodontic bracket 148 in accordance with the present invention illustrating the arch wire opening in a gingival orientation and its difference in width from the diameter of the arch wire slot within the bracket body (indicated with dashed lines). FIG. 15 shows a top plan view of a preferred embodiment of a static self-ligating orthodontic bracket 150 in accordance with the present invention illustrating the arch wire opening in a facial orientation and its difference in width from the diameter of the arch wire slot within the bracket body (indicated with dashed lines). FIG. 16 shows a side view of a preferred embodiment of the static self-ligating orthodontic bracket 152 in accordance with the present invention, with the arch wire opening in a labial orientation.

Figure 17:
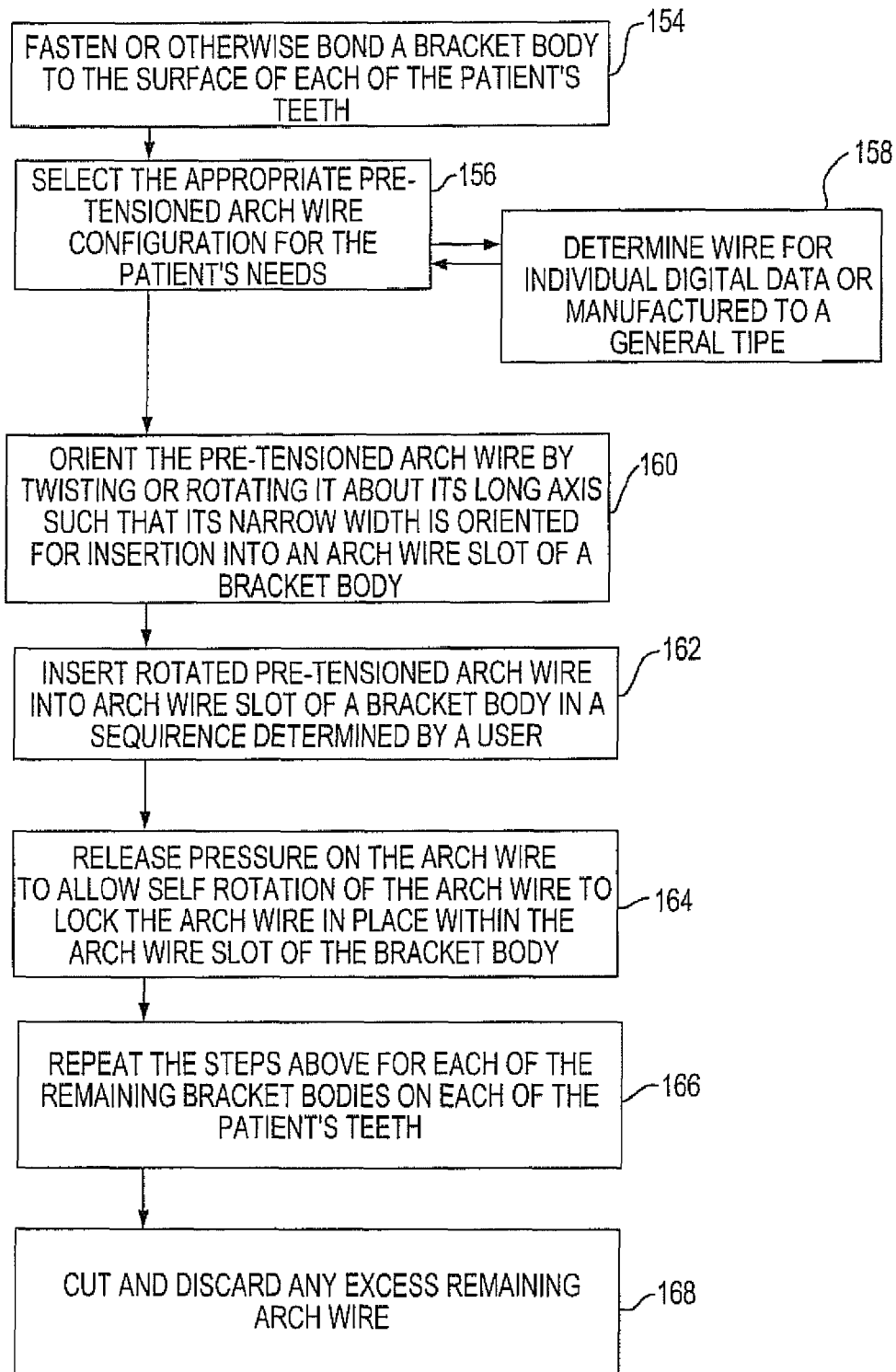
FIG. 17 shows a flow diagram illustrating the method of applying the static self-ligating orthodontic bracket and pre-tensioned arch wire, preferably for use in straightening or otherwise moving teeth of a patient, in accordance with the present invention.

Referring last to FIG. 17, shown is a flow diagram illustrating the method of applying the static self-ligating orthodontic bracket and pre-tensioned arch wire, preferably for use in straightening or otherwise moving teeth of a patient, in accordance with the present invention. As depicted, a practitioner or user first fastens or otherwise bonds a bracket body 40 to the surface of each of the patient's teeth (step 154). The practitioner then selects the appropriate pre-tensioned arch wire 44 configuration for the particular patient's needs (step 156). Once all of the bracket bodies 40 have been attached and are ready to receive the arch wire 44, the practitioner applies a local force to orient the pre-tensioned arch wire 44 to the slot (prior to insertion into the slot) of the bracket body 40. The practitioner orients the straightened pre-tensioned arch wire 44 (in a local position) by twisting or rotating it about its long axis such that its narrow width is oriented for insertion into arch wire slot of a first bracket body (step 160) (see also FIGS. 3A and 3B). The rotated straightened pre-tensioned arch wire 44 is then inserted into arch wire slot 48 of a first bracket body 40 through the opening 46 therein (step 162) (see also FIG. 3C). It will be noted that in a separate step (optional step 158) a user determines a suitable individual patient wire by captured digital data or selects a wire manufactured to a general type and suitable to a patient.

Once the arch wire 44 is fully inserted into arch wire slot 48 the practitioner has released the arch wire periodically throughout the insertion steps and now fully releases the arch wire, the wire twists itself (to release tension) along the long axis (a clockwise or counterclockwise moment to the arch wire 44) to lock the arch wire 44 in place within the arch wire slot 48 of the bracket body 40 (step 164) (see also FIGS. 3D and 3E). The manufactured shape of the wire determines how much the wire twists and what forces will be applied to the brackets and teeth respectively. Necessarily, to complete the process, the practitioner would repeat the insert-release above steps above for each of the bracket bodies 40 on each of patient's teeth (step 166). Finally, any excess arch wire 44 would be cut and discarded (step 168). Once finished, each bracket body 40 has arch wire 44 locked in position within the arch wire slots 48 (see FIG. 3F).

In the claims, means or step-plus-function clauses are intended to cover the structures described or suggested herein as performing the recited function and not only structural equivalents but also equivalent structures. Thus, for example, although a nail, a screw, and a bolt may not be structural equivalents in that a nail relies on friction between a wooden part and a cylindrical surface, a screw's helical surface positively engages the wooden part, and a bolt's head and nut compress opposite sides of a wooden part, in the environment of fastening wooden parts, a nail, a screw, and a bolt may be readily understood by those skilled in the art as equivalent structures.

Having described at least one of the preferred embodiments of the present invention with reference to the accompanying drawings, it is to be understood that such embodiments are merely exemplary and that the invention is not limited to those precise embodiments, and that various changes, modifications, and adaptations may be effected therein by one skilled in the art without departing from the scope or spirit of the invention as defined in the appended claims. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A static self-ligating orthodontic bracket system, for coupling
   an arch wire with a tooth, wherein said system comprises:
   a bracket body configured to be mounted to a tooth;
   an arch wire slot configured for receiving the arch wire in a tensioned configuration therein, said arch wire slot forming an enclosed space having an access opening for pass through of said arch wire, said arch wire slot configured with a plurality of protruding stops on an interior wall surface on an inner perimeter thereof, said stops spaced apart from one another, said stops comprising at least a first and a second stop that are positioned at opposed positions relative to one another along the interior wall surface, said stops defining a space therebetween along the interior surface, the space being generally smooth; and
   a slot opening for receiving said arch wire into said arch wire slot, said slot opening having a width less than a dimension of said arch wire slot, the stops being spaced apart from the slot opening, wherein said arch wire is configured with a non-circular cross-section for secure lodgment within said arch wire slot during a use of said system, said arch wire having shape memory properties and having a long axis, said arch wire being configured to be twisted about the long axis to assume the tensioned configuration and to be inserted into said arch wire slot through said slot opening when in the tensioned configuration, said arch wire being configured to twist itself and to transition to an untensioned configuration within said arch wire slot and to be locked within said arch wire slot.

2. The bracket system according to claim 1, wherein said arch wire slot has a generally round cross-sectional configuration.

3. The bracket system according to claim 1, wherein said arch wire has a cross-sectional configuration selected from the group consisting of oval, rectangular, oblong, eccentric shape, egg-shaped and kidney-shaped.

4. The bracket system according to claim 1, wherein said arch wire slot has a cross-sectional configuration selected from the group consisting of oval, rectangular, oblong, egg-shaped, irregular and kidney-shaped.

5. The bracket system according to claim 1, wherein said bracket body is made from a material selected from the group consisting of metal, composites of metals, composites of ceramics, ceramic and polymer.

6. The bracket system according to claim 1, wherein said bracket body further comprises:
an additional tie wing positioned on an upper end and a lower end thereof.

7. The bracket system according to claim 1, wherein said slot opening is configured to open in a gingival orientation.

8. The bracket system according to claim 1, wherein said slot opening is configured to open in a facial orientation.

9. The bracket system according to claim 1, wherein said slot opening is configured to open in a labial orientation.

10. A method, for coupling an arch wire with a tooth using a static self-ligating orthodontic bracket system, comprising the steps of:
fastening a bracket body configured to be mounted to a surface of said tooth;
an arch wire slot of said bracket body configured for receiving an arch wire therein, said arch wire having shape memory properties and is transitionable between a tensioned configuration and an untensioned configuration, said arch wire being received in said arch wire slot when in the tensioned configuration, said arch wire slot forming an enclosed space having an access opening for pass through of said arch wire, said arch wire slot configured with a plurality of protruding stops in an interior wall surface on an inner perimeter thereof, said stops spaced apart from one another, said stops comprising at least a first and a second stop that are positioned at opposed positions relative to one another along the interior wall surface, said stops defining a space therebetween along the interior surface, the space being generally smooth;
a slot opening of said bracket body for receiving said arch wire in the tensioned configuration into said arch wire slot, said slot opening having a width less than a dimension of said arch wire slot, the stops being spaced apart from the slot opening;
selecting an appropriate pre-tensioned arch wire for application to a bracket;
said arch wire being configured with a non-circular cross-section for secure lodgment within said arch wire slot during a use of said method;
applying a local force to orient said pre-tensioned arch wire;
orienting said arch wire in a straightened configuration for insertion into said arch wire slot of said bracket body, said step of orienting including rotating said arch wire about its long axis in a first direction and orienting its narrow width for insertion into said arch wire slot though said slot opening;
inserting said arch wire in the straightened configuration into said arch wire slot of said bracket body; and
releasing said local force to said arch wire while said arch wire is within thereby allowing said arch wire to rotate relative to said arch wire slot to lock said arch wire in place within said arch wire slot of said bracket body as said arch wire is transitioned to said untensioned configuration.

11. The method according to claim 10, wherein said arch wire has a cross-sectional configuration selected from the group consisting of oval, rectangular, oblong, egg-shaped and kidney-shaped.

12. The method according to claim 10, wherein said bracket body is made from a material selected from the group consisting of metal, ceramic and polymer.

13. The method according to claim 10, wherein said arch wire slot has a round cross-sectional configuration.

14. The method according to claim 10, wherein said arch wire slot has a cross-sectional configuration selected from the group consisting of oval, rectangular, oblong, egg-shaped, irregular and kidney-shaped.

* * * * *